(12) United States Patent
Richert et al.

(10) Patent No.: US 11,415,150 B2
(45) Date of Patent: Aug. 16, 2022

(54) FLUID PUMP

(71) Applicant: Berlin Heart GmbH, Berlin (DE)

(72) Inventors: Hendryk Richert, Berlin (DE); Graham Foster, Swansea (GB)

(73) Assignee: Berlin Heart GmbH, Berlin (DE)

( * ) Notice: Subject to any disclaimer, the term of this patent is extended or adjusted under 35 U.S.C. 154(b) by 0 days.

(21) Appl. No.: 17/058,509

(22) PCT Filed: May 27, 2019

(86) PCT No.: PCT/EP2019/063678
§ 371 (c)(1),
(2) Date: Nov. 24, 2020

(87) PCT Pub. No.: WO2019/228998
PCT Pub. Date: Dec. 5, 2019

(65) Prior Publication Data
US 2021/0199127 A1 Jul. 1, 2021

(30) Foreign Application Priority Data

May 28, 2018 (EP) .................................... 18174614
Oct. 18, 2018 (EP) .................................... 18201263

(51) Int. Cl.
*F04D 29/52* (2006.01)
*A61M 60/237* (2021.01)
(Continued)

(52) U.S. Cl.
CPC ........... *F04D 29/528* (2013.01); *A61M 60/17* (2021.01); *A61M 60/221* (2021.01);
(Continued)

(58) Field of Classification Search
CPC .......... A61M 2210/125; A61M 60/122; A61M 60/148; A61M 60/205; A61M 60/40;
(Continued)

(56) References Cited

U.S. PATENT DOCUMENTS 3,354,833 A * 11/1967 Laing .................... F16C 25/045
417/353
3,647,324 A * 3/1972 Rafferty .............. A61M 60/422
417/420
(Continued)

FOREIGN PATENT DOCUMENTS

DE 199 44 863 A1 4/2001
WO WO 98/04834 A1 2/1998
WO WO-2016187057 A1 * 11/2016 ............ A61M 60/82

OTHER PUBLICATIONS

International Search Report with English translation, issued in International Application No. PCT/EP2019/063678, dated Jul. 31, 2019, pp. 1-8, European Patent Office, Rijswijk, Netherlands.

*Primary Examiner* — Kenneth Bomberg
*Assistant Examiner* — Adam W Brown
(74) *Attorney, Agent, or Firm* — Crowell & Moring LLP

(57) ABSTRACT

A fluid pump for conveying a fluid is provided comprising: a housing with a fluid inlet and a fluid outlet, a rotor which is disposed rotatably about an axis of rotation in the housing, and a rotor body and at least one conveying element connected rigidly to the rotor body in order to convey the fluid from the fluid inlet to the fluid outlet, the rotor being mounted in the housing radially to the axis of rotation by means of a passive magnetic bearing and also axially and radially by means of a mechanical and/or hydrodynamic bearing disposed on the inlet side or outlet side. A safety bearing is disposed on one side of the rotor situated opposite the mechanical and/or hydrodynamic bearing, wherein the safety bearing has a first safety bearing component connected rigidly to the rotor and a second safety bearing component connected rigidly to the housing.

18 Claims, 4 Drawing Sheets

(51) Int. Cl.
| | |
|---|---|
| *A61M 60/226* | (2021.01) |
| *A61M 60/419* | (2021.01) |
| *A61M 60/221* | (2021.01) |
| *A61M 60/824* | (2021.01) |
| *A61M 60/825* | (2021.01) |
| *A61M 60/82* | (2021.01) |
| *F04D 29/047* | (2006.01) |
| *F04D 29/18* | (2006.01) |
| *A61M 60/17* | (2021.01) |
| *A61M 60/818* | (2021.01) |
| *A61M 60/816* | (2021.01) |
| *F04D 15/00* | (2006.01) |

(52) U.S. Cl.
CPC ........ *A61M 60/226* (2021.01); *A61M 60/237* (2021.01); *A61M 60/419* (2021.01); *A61M 60/816* (2021.01); *A61M 60/818* (2021.01); *A61M 60/82* (2021.01); *A61M 60/824* (2021.01); *A61M 60/825* (2021.01); *F04D 15/0088* (2013.01); *F04D 29/0476* (2013.01); *F04D 29/181* (2013.01); *A61M 2205/0238* (2013.01); *A61M 2205/3317* (2013.01); *A61M 2205/3327* (2013.01)

(58) Field of Classification Search
CPC .............. A61M 60/416; A61M 60/812; A61M 60/814; A61M 60/82; F04D 13/06; F04D 29/041; F04D 29/048; F04D 29/18; F04D 29/186; F04D 7/00
See application file for complete search history.

(56) References Cited

U.S. PATENT DOCUMENTS

| | | | | |
|---|---|---|---|---|
| 4,984,972 | A * | 1/1991 | Clausen | F04D 29/628 417/420 |
| 5,507,629 | A * | 4/1996 | Jarvik | A61M 60/82 417/423.3 |
| 5,840,070 | A * | 11/1998 | Wampler | F16C 39/063 604/131 |
| 6,155,969 | A * | 12/2000 | Schima | F16C 32/0423 600/16 |
| 6,581,476 | B1 | 6/2003 | Fremerey | |
| 6,761,532 | B2 * | 7/2004 | Capone | A61M 60/82 415/200 |
| 9,616,157 | B2 * | 4/2017 | Akdis | F04D 29/0473 |
| 10,195,324 | B2 * | 2/2019 | Foster | A61M 60/818 |
| 10,660,996 | B2 * | 5/2020 | Foster | A61M 60/82 |
| 10,780,207 | B2 * | 9/2020 | Dur | A61M 60/419 |
| 2015/0285258 | A1 * | 10/2015 | Foster | F04D 17/10 415/203 |
| 2020/0368415 | A1 * | 11/2020 | Antaki | F16C 32/0425 |

\* cited by examiner

FLUID PUMP

CROSS-REFERENCE TO RELATED APPLICATIONS

This application is a 371 nationalization of international patent application PCT/EP2019/063678 filed May 27, 2019, which claims priority under 35 USC § 119 to European patent application EP 18174614.0, filed May 28, 2018 and to European patent application EP 18201263.3 filed Oct. 18, 2018. The entire contents of each of the above-identified applications are hereby incorporated by reference.

BRIEF DESCRIPTION OF THE DRAWINGS

There are shown

DETAILED DESCRIPTION

Figure 1:
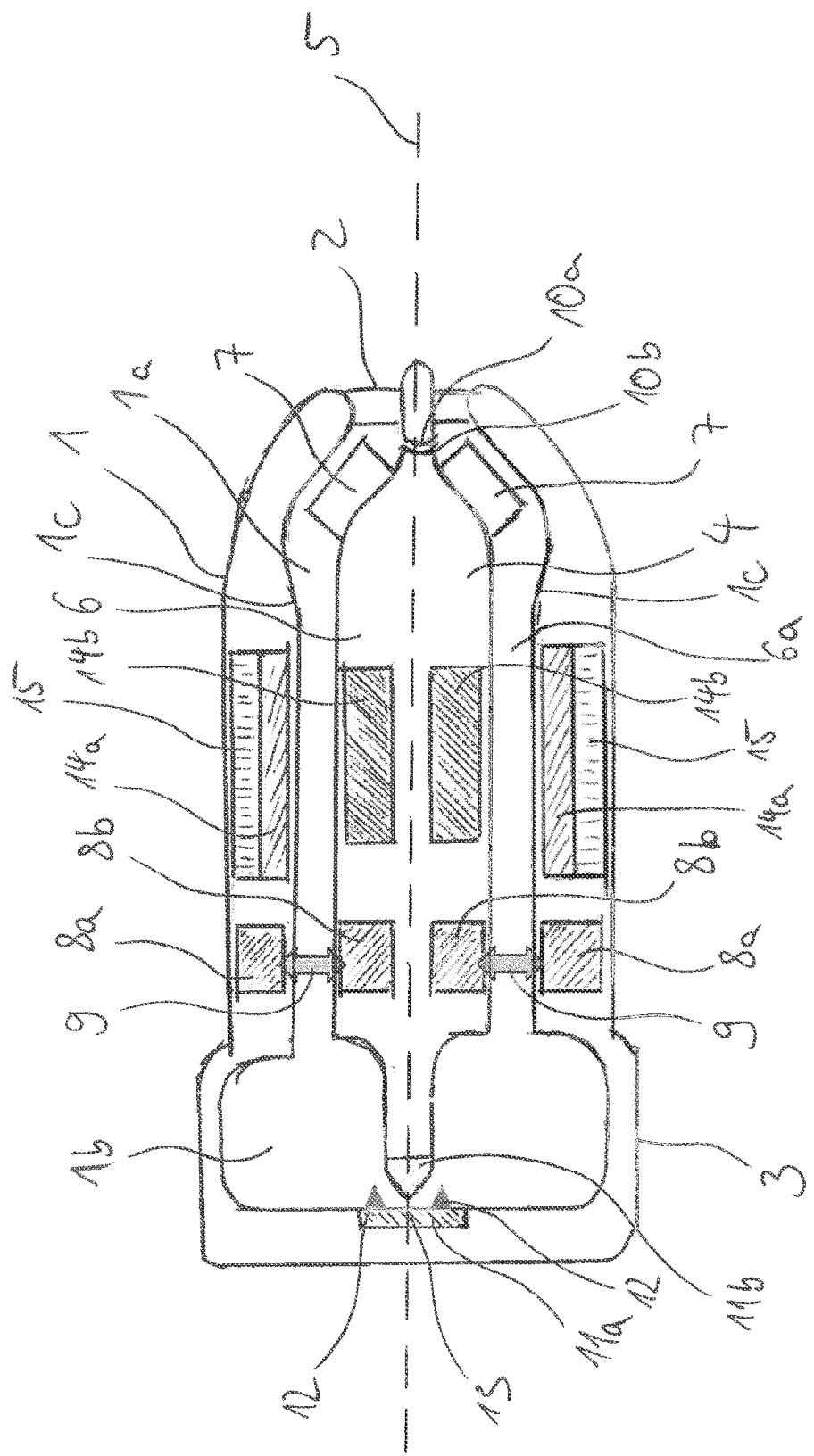
FIG. 1 a first embodiment of a fluid pump according to the invention in an axial section view, FIG. 2 a second embodiment of a fluid pump according to the invention in an axial section view, FIG. 3 a third embodiment of a fluid pump according to the invention in an axial section view, FIG. 4 a diagram which illustrates the protection from contact by the safety bearing, FIG. 5 a fourth embodiment of a fluid pump according to the invention, and FIG. 6 a fifth embodiment of a fluid pump according to the invention.

The invention relates to a fluid pump for conveying a fluid, in particular blood.

In the state of the art, blood pumps having hydrodynamic, magnetic and mechanical bearing systems and also combinations thereof are known. Furthermore, hybrid bearing systems having a passively magnetic bearing and a mechanical bearing are known. In particular, two magnetic radial bearings with an axial degree of freedom, which is fixed by two mechanical (support) bearings, are thereby used.

A further popular form of blood pumps has two mechanical bearings which can be configured as spherical, conical or tapered axial bearings and have the disadvantage that it is practically impossible, on the one hand, to adjust the axial bearing gaps such that they are small enough in order that no blood or only a specific proportion of the blood can penetrate into the bearings. Furthermore, the bearing gaps do not remain constant during operation of the blood pump but rather change as a result of wear. If blood penetrates into the bearing gaps, it is subjected to strong shearing forces and is damaged or destroyed by for example haemolysis, platelet activation and other negative effects. On the other hand, the bearing gaps in these mechanical bearings also cannot be enlarged such that shearing forces are reduced since the enlargement of the axial gap leads to instabilities during operation of the pump.

Pumps which are mounted completely actively magnetically have the disadvantage that they have large and complex constructions. A related state of the art is described in the publication U.S. Pat. No. 5,507,629 A. This publication relates to artificial hearts which are small enough to be implanted in the natural heart. The total radial load of a high-speed pump rotor and the large part of the axial load are supported by a radially stable arrangement of permanent magnets. A pressure-bearing contact point is provided, which uses an ultrahard, wear-resistant material, preferably diamond. This publication does not disclose a safety bearing.

The object of the present invention is therefore to provide a fluid pump for conveying a fluid, in particular blood, which has a small and simple construction, minimises blood damage and has high efficiency.

The fluid pump according to the invention for conveying a fluid, in particular blood, comprises a housing with a fluid inlet and a fluid outlet, a rotor which is disposed rotatably about an axis of rotation in the housing, and a rotor body and at least one conveying element connected rigidly to the rotor body in order to convey the fluid from the fluid inlet to the fluid outlet, the rotor being mounted in the housing radially to the axis of rotation by means of a passive magnetic bearing and also axially and radially by means of a mechanical and/or hydrodynamic bearing disposed on the inlet side or outlet side.

There is understood by a mechanical and/or hydrodynamic bearing, on the one hand, purely mechanical bearings or purely hydrodynamic bearings and also, on the other hand, bearings which have both mechanical and hydrodynamic bearing features. For example, the mechanical and/or hydrodynamic bearing can be configured as mechanical ball-and-cup bearing, a fluid film which makes in addition a hydrodynamic contribution to the bearing being present between two bearing components of the ball-and-cup bearing.

The fluid pump according to the invention is distinguished by a safety bearing being disposed on one side of the rotor situated opposite the mechanical and/or hydrodynamic bearing, which safety bearing has a first safety bearing component connected rigidly to the rotor and a second safety bearing component connected rigidly to the housing, during operation of the fluid pump, an axial and radial spacing between the first and the second safety bearing component being greater than a radial minimal spacing between the rotor and the housing, and the safety bearing being equipped to restrict deflection of the rotor in the radial direction inside the housing.

In the case of the present fluid pump according to the invention, all degrees of freedom are fixed in fact by the axially and radially acting mechanical and/or hydrodynamic bearing and the radially acting magnetic bearing. With the help of the magnetic bearing, the rotor can be pretensioned in addition either towards the mechanical and/or hydrodynamic bearing or away from the mechanical and/or hydrodynamic bearing in order to increase or to reduce the force in the bearing or the bearing gap. The mechanical and/or hydrodynamic bearing can be impinged upon in this way with a defined force so that said bearing operates in a stable manner under normal conditions. Because of the constant pretension of the magnetic bearing (within the scope of the wear and tear to be expected over the pump lifespan in the mechanical support bearing), the axial positon of the rotor adapts dynamically to any change in the bearing geometry in the mechanical and/or hydrodynamic bearing so that the bearing gap in the mechanical and/or hydrodynamic bearing is always optimised during the pump lifespan such that a desired proportion of the fluid conveyed by the fluid pump or no fluid can penetrate into the mechanical and/or hydrodynamic bearing. Furthermore, the safety bearing serves to prevent an axial and/or radial falling-out of the rotor from the bearing system if great interfering forces act on the rotor which could overcome the retaining force of the magnetic bearing. The safety bearing can retain the rotor axially and radially and hence prevent any contact of more sensitive rotor components, such as e.g. the conveying element, with the housing. As a result of the fact that the safety bearing is disposed opposite and hence far away from the mechanical and/or hydrodynamic bearing, the bearing clearance in the safety bearing, i.e. a spacing between the safety bearing components, can be chosen to be relatively large despite a small clearance between the conveying element and the housing. As a result, in fact the fluid flowing through the fluid pump can penetrate into the safety bearing but, because of the large bearing clearance, the shearing forces acting on the fluid are low. The small clearance between the conveying element and the housing increases the efficiency of the fluid pump. Hence the fluid pump according to the invention enables efficient conveyance of a fluid, preventing striking of the rotor on the housing and reducing a risk of fluid damage, such as, in the case of blood, blood damage.

As passive magnetic bearing, in principle any type of repellent magnetic bearing can be used. In particular however, magnetic bearings consisting of a plurality of axially anti-parallel magnetised permanent magnets are particularly suitable for this application as so-called squeeze-field arrays and also Halbach arrays with the combination of axially and radially magnetised magnets.

In an advantageous embodiment of the invention, the magnetic bearing can be disposed in the axial direction on a side of the rotor body situated towards the safety bearing. In this way, the spacing from a rotational point of the mechanical and/or hydrodynamic bearing is large and less force is required in order to retain the rotor in its central position with respect to the radial direction between the bearings.

The magnetic bearing can have at least one first and one second magnet, the first magnet being disposed in the housing and the second magnet being disposed in the rotor body, the second magnet opposite the first magnet being able to be disposed offset in the axial direction towards the mechanical and/or hydrodynamic bearing such that the rotor body can be pretensioned directed in the axial direction towards the mechanical and/or hydrodynamic bearing and/or counter to a fluid flow.

The mechanical and/or hydrodynamic bearing can have a first bearing component connected rigidly to the rotor and a second bearing component connected rigidly to the housing, and the magnetic bearing can be configurable such that, during operation of the fluid pump, a spacing between the first and the second bearing component is minimised and hence is smaller than the axial and/or radial spacing between the first safety bearing component and the second safety bearing component.

The safety bearing can furthermore be configured such that, during operation of the fluid pump, there is, between the first and the second safety bearing component, an axial spacing of ≥10 µm and/or ≤500 µm, in particular of ≥50 µm and/or ≤150 µm and a radial spacing of ≥50 µm and/or ≤1,000 µm, in particular of ≥150 µm and/or ≤500 µm. The axial and radial spacing have a size at which lower shearing forces act on the fluid penetrating into the bearing gap of the safety bearing than with bearing gaps in mechanical and/or hydrodynamic bearings which serve as main bearings. Furthermore, the axial and radial bearing gap are situated close to or on the axis of rotation, where low tangential speeds and therefore low shearing forces prevail. Hence the safety bearing represents, on the one hand, a defined and more reliable limit stop for the rotor without, on the other hand, being a source of damage to the fluid.

Furthermore, it is particularly preferred if the safety bearing is disposed in the fluid pump such that a spacing between the mechanical and/or hydrodynamic bearing and the safety bearing is maximal, in particular more than twice as large as a spacing between the mechanical and/or hydrodynamic bearing and the conveying element. In this case, the safety bearing is far away from the mechanical and/or hydrodynamic bearing and hence far away from the rotational point of the mechanical and/or hydrodynamic bearing, about which the rotor can be deflected by external interfering forces, such as e.g. a g-force (force which acts on the fluid pump in the case of acceleration of the fluid pump), if the interfering forces overcome the retaining force of the magnetic bearing. Because of the large spacing from this rotational point, there can be provided, with the same angle difference of the axis of rotation relative to the central position of the rotor in the safety bearing, a larger radial spacing between the safety bearing components than with a safety bearing disposed nearer the rotational point, which causes a reduction of shearing forces in the safety bearing. Furthermore, in this way a low clearance between a conveying element disposed close to the mechanical and/or hydrodynamic bearing and the housing can be made possible, which increases the efficiency of the fluid pump since the safety bearing offers sufficient limit-stop protection.

In a further advantageous embodiment of the invention, the safety bearing can also be disposed outside a primary fluid path leading from the fluid inlet to the fluid outlet, and hence outside a primary fluid flow, in particular the safety bearing can be disposed on one side of a volute of the housing orientated away from the mechanical and/or hydrodynamic bearing. In particular, also the magnetic bearing can be disposed on one side of the volute orientated away from the mechanical and/or hydrodynamic bearing outside the primary fluid path. The advantage of this arrangement of the magnetic bearing resides in the fact that the magnetic bearing can have a smaller configuration since magnetic bearing components of the magnetic bearing can be disposed more closely beside each other and thus, also because of smaller magnets, a sufficiently large magnetic force is producible to retain the rotor in the predetermined position. Because of the enlarged spacing between magnetic bearing and the rotational point of the mechanical and/or hydrodynamic bearing, the magnetic bearing can in addition produce a greater lever effect in the radial direction of the mechanical and/or hydrodynamic bearing and thus retain the rotor in the predetermined position with lower force expenditure.

It is advantageous if the conveying element is disposed in a region of the rotor body adjacent to the mechanical and/or hydrodynamic bearing. As a result, a relatively free tilting of the rotor from its central position relative to the radial direction is possible despite a small spacing of the conveying element from the housing.

It is particularly advantageous if the conveying element is disposed on the rotor body such that the conveying element overlaps the mechanical and/or hydrodynamic bearing radially to the axis of rotation. In this case, the conveying element, on the one hand, can be disposed about the rotational point of the mechanical and/or hydrodynamic bearing which enables free tilting of the rotor from its central position without touching the housing. On the other hand, the conveying element can have a large configuration relative to the rotor body, which enables higher efficiency of the fluid pump.

Furthermore, it can be advantageous to dispose the conveying element in a region of the rotor body in which a spacing between a surface of the rotor body and the housing is greater than a minimal spacing between the surface and the housing. In particular, the conveying element can be disposed in a volute of the housing. As a result, the conveying element can have a larger configuration, which increases the efficiency of the fluid pump, and the danger of the conveying element touching on the housing can be reduced since the volute has a large free volume relative to the remaining part of the fluid pump.

Normally, the rotor can have a multitude of conveying elements. In particular, a partial quantity of the multitude of conveying elements can then be disposed adjacent to the mechanical and/or hydrodynamic bearing and a further partial quantity of the multitude of conveying elements in a volute of the housing. This increases the efficiency of the fluid pump.

It is particularly preferred if the conveying element has a length and/or a width of ≥2 mm and/or ≤20 mm, in particular ≥5 mm and/or ≤10 mm.

In a further advantageous embodiment of the invention, the conveying element can have, on one side orientated towards the housing, an axial section contour which is adapted to an inner axial section contour of the housing on a side of the housing orientated towards the conveying element so that a radial spacing between the conveying element and the housing, along at least one region of the conveying element, is essentially constant in the axial direction, in particular at least over ≥40%, ≥50% or ≥80% of a length of the conveying element in the axial direction. This increases in particular the efficiency of the fluid pump and can assist free tilting of the rotor.

A relatively free tilting of the rotor is possible in particular when the axial section contour of the conveying element and the inner axial section contour of the housing have corresponding spherical curves, in particular in the case in which the conveying element is disposed adjacent to or about the rotational point of the mechanical and/or hydrodynamic bearing.

Furthermore, it is advantageous if the safety bearing has a rotational-symmetrical configuration about the axis of rotation of the rotor, a maximum diameter of the safety bearing being smaller than a maximum diameter of the rotor. The nearer the bearing gap of the safety bearing is situated to the axis of rotation, the smaller is a tangential speed of the fluid penetrating into the safety bearing. As a result, also the shearing forces exerted on the fluid by the safety bearing components are lower.

The mechanical and/or hydrodynamic bearing can be in particular a spherical bearing, a ball-and-cup bearing and/or a conical bearing.

The fluid pump can be an axial flow pump or a radial flow pump or a combination of axial flow- and radial flow pump.

The first and/or the second safety bearing component and/or the first and/or the second safety bearing component of the mechanical and/or hydrodynamic bearing can comprise a ceramic, polymeric, metallic and/or monocrystalline material or consist thereof.

Furthermore, the first and/or second safety bearing component and/or the first and/or second bearing component of the mechanical and/or hydrodynamic bearing can have a coating which inhibits wear and tear and/or reduces blood damage, in particular reduces haemolysis. The coating can comprise in particular silicones, PU, MPC, multiple sugars, general polymers, ceramics, diamond-like materials, metal layers, nitrides, oxides, multiple layers, bioactive, medicine-containing and/or other layers or consist thereof.

In the following, several embodiments of a fluid pump according to the invention are described in more detail on the basis of Figures. Various elements which are essential to the invention or which enhance it advantageously are mentioned within the scope respectively of a concrete example, also individual ones of these elements being able to be used as such for development of the invention—also detached from the context of the example and from further features of the example. Furthermore, the same or similar reference numbers are used for the same or similar elements and explanation thereof is therefore partially omitted.

FIG. 1 shows a first embodiment of a fluid pump according to the invention in an axial section view. The fluid pump has a housing 1 which has an essentially hollow-cylindrical outer form which is essentially rotational-symmetrical about a central axis 5 of the housing 1. The housing 1 has an interior 1a configured to be hollow-cylindrical, which is delimited by an inner wall 1b of the housing 1. Furthermore, the housing 1 has a fluid inlet 2 on one side of the housing 1 in the region of the central axis 5. On the side of the housing 1 opposite the fluid inlet 2, the housing 1 has a volute 1b which is configured as a spiral extension of the housing 1. By means of the housing 1, a fluid can be guided from the fluid inlet 2 along the central axis 5 to the volute 1b. Inside the volute 1b, the fluid is no longer guided along the central axis 5 but firstly radially away from the central axis 5 and then around the central axis 5 to a fluid outlet 3 disposed in the volute 1b (the fluid outlet 3 here is not illustrated directly, the reference number 3 indicates merely a possible position of the fluid outlet). The fluid outlet 3 is disposed in the spiral volute 1b such that the fluid can emerge through the fluid outlet 3 tangentially to the central axis 5 out of the housing 1. Furthermore, a rotor 4 with a rotor body 6 is disposed in the housing 1. The rotor 4 is mounted in the region of the fluid inlet 2 by means of a mechanical and/or hydrodynamic bearing 10a, 10b. Furthermore, the fluid pump has a passive magnetic bearing 8a, 8b which is disposed in a region of the fluid pump situated towards the volute 1b and has a housing magnet 8a and a rotor magnet 8b. Both the housing magnet 8a and the rotor magnet 8b have cylindrical or hollow-cylindrical configurations and are disposed concentrically relative to each other and about the central axis 5 of the housing 1. The magnetic bearing 8a, 8b retains the rotor 5 on the central axis 5 of the housing 1 so that an axis of rotation of the rotor 4 coincides with the central axis 5 of the housing 1. The magnets of the magnetic bearing 8a, 8b concern repellent magnets which retain the rotor on the central axis 5 by means of a repellent magnetic force 9 acting in the radial direction. The mechanical and/or hydrodynamic bearing is configured as a spherical bearing and has a first bearing component 10a connected rigidly to the housing 1 and a second bearing component 10b connected rigidly to the rotor 4. The bearing component 10a has a spherical or generally convex configuration in the region situated towards the bearing component 10b whilst the bearing component 10b has a cup-shaped or generally concave configuration in a region situated towards the bearing component 10a. It is thereby irrelevant on which side the convex form sits. Among convex or concave there are also non-constant shapes, such as e.g. frustoconical or stepped bearings. Hence, the mechanical and/or hydrodynamic bearing 10a, 10b restricts a translatory movement of the rotor 4 in the axial direction in the direction of the fluid inlet 2 and in the radial direction. The magnetic bearing 8a, 8b can be configured such that the rotor 4 can be pressed into the mechanical and/or hydrodynamic bearing 10a, 10b during operation of the fluid pump or relieves the load of the mechanical and/or hydrodynamic bearing counter to the occurring fluid forces during operation. In the design of the magnetic bearing 8a, 8b, a potential pretension of the rotor 4 against a fluid flow through the fluid pump should therefore be jointly included. As a result of the thrust of the magnetic bearing 8a, 8b on the rotor 4, which is large enough to press the rotor, during operation of the fluid pump, always into the mechanical and/or hydrodynamic bearing, it is avoided that, during operation of the fluid pump, the bearing gap between the bearing components 10a and 10b is enlarged, for example by wear and tear. The bearing gap between the bearing components 10a, 10b is hence always minimised by the magnetic bearing 8a, 8b, as a result of which it is prevented that larger components of the fluid, which can be for example in the case of blood, erythrocytes or other cells or proteins, pass between the bearing components 10a, 10b and are damaged or destroyed there. On one side of the fluid pump opposite the mechanical and/or hydrodynamic bearing, in the region of the fluid outlet 3, a safety bearing 11a, 11 b is disposed in the volute 1b having a first safety bearing component 11a connected rigidly to the housing 1 and a second safety bearing component 11b connected rigidly to the rotor 4. During normal operation of the fluid pump, no contact takes place between the safety bearing component 11a and the safety bearing component 11b. Rather, the rotor 4 can move freely inside the safety bearing 11a, 11b. If now external interfering forces occur, such as e.g. under acceleration of the fluid pump, the result can be a severe deflection of the rotor 4 about the mechanical and/or hydrodynamic bearing 10a, 10b. The mechanical and/or hydrodynamic bearing 10a, 10b represents a rotational point for the rotor 4. In order to limit this deflection, the safety bearing component 11a has a hollow-cylindrical (concave), radial delimiting element 12 which represents a radial limit stop for the bearing component 11b, here also the side for the concave safety bearing component being irrelevant. Furthermore, the safety bearing component 11a has an axial limit stop 13 which prevents the rotor 4 from falling out entirely of the mechanical and/or hydrodynamic bearing 10a, 10b in the axial direction in the direction of the volute 1b. Since the safety bearing 11a, 11 b concerns a contactless safety bearing, a bearing gap in the safety bearing, i.e. a spacing between the first and the second safety bearing component 11a, 11b, can be chosen to be so large that in fact fluid can pass between the safety bearing components 11a and 11b, however, at the same time also the shearing forces on the fluid prevailing in the safety bearing 11a, 11 b are low. Hence, the safety bearing 11a, 11b, on the one hand, enables security against contact of sensitive components of the rotor 4 with simultaneously low fluid damage due to shearing forces. Furthermore, in contrast to the fluid pumps of the state of the art, in the present fluid pump according to the invention it is not necessary to adjust the bearing gap in the safety bearing 11a, 11 b exactly or always to minimise it in order to prevent penetration of fluid into the bearing gap since contact with the safety bearing 11a, 11 b does not damage the fluid. Furthermore, the radial delimiting element 12 and the axial limit stop 13 of the safety bearing 11a, 11 b can be separated and the rotor 4 can be delimited radially shortly before the volute 1b by protruding elements which can also develop a conveying effect. Struts, bucket elements, rings or ring segments are conceivable here. Furthermore, the fluid pump according to the invention can be constructed and miniaturised easily since merely a passive magnetic bearing is used.

In addition, the rotor 4 has, adjacent to the fluid inlet 2, conveying elements 7 which convey the fluid after entering through the fluid inlet 2 along the central axis 5 in the direction of the fluid outlet 3. The external contour of the conveying elements 7 orientated towards the housing 1 is adapted to the contour of the inner wall 1c of the housing 1 such that a small spacing (clearance of the conveying element 7) between the conveying element 7 and the inner wall 1c is produced. A small clearance of the conveying element 7 prevents the fluid from flowing past the conveying element 7 or from not being reached by the conveying element 7 and being accelerated in the direction of the fluid outlet 3. A small clearance between conveying element 7 and housing 1 hence increases the efficiency of the fluid pump. Furthermore, adjacent to the fluid inlet 2, the inner wall 1c is configured spherically around the conveying element 7 so that, in this region, the rotor 4 can tilt freely over as large an angle range as possible about the rotational point of the mechanical and/or hydrodynamic bearing 10a, 10b. As a result, early contact of the conveying elements 7 on the housing 1 is prevented and contact of the rotor 4 is effected only at the delimiting element 12 of the safety bearing 11a, 11b.

The rotor 4 is driven by means of a motor stator 14a, 15a disposed in the housing 1 and by means of a motor magnet 14b disposed in the rotor body 6. The motor stator 14a, 15 and the motor magnet 14b are disposed concentrically to each other.

Figure 2:
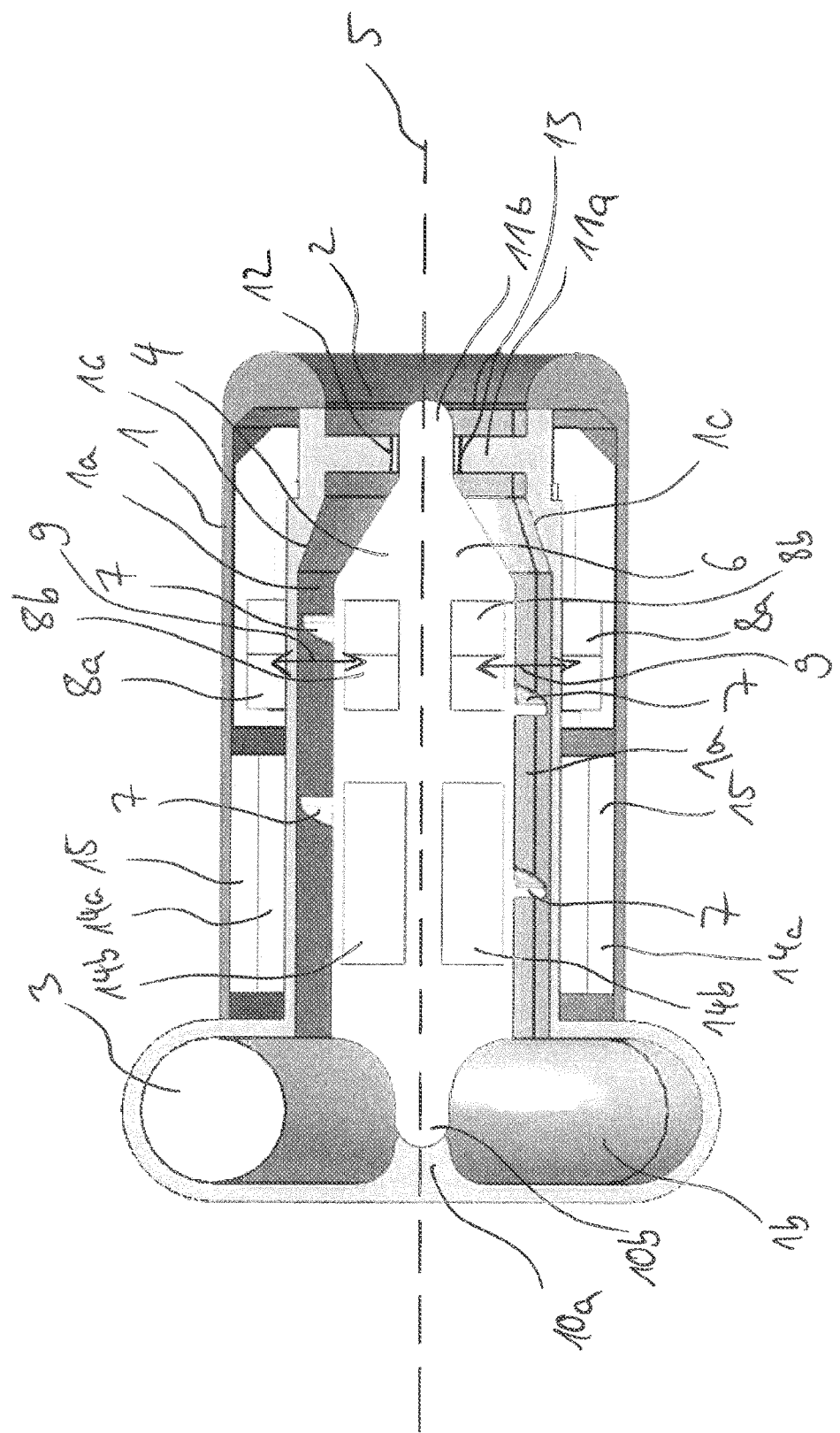

FIG. 2 shows a further embodiment of a fluid pump according to the invention in an axial section view. In contrast to the first embodiment of FIG. 1, in the fluid pump in FIG. 2, the mechanical and/or hydrodynamic bearing 10a, 10b is disposed in the volute 1b and the safety bearing 11a, 11 b in the region of the fluid inlet 2. Correspondingly, the radial magnetic bearing 8a, 8b is disposed in a front region, i.e. situated towards the fluid inlet 2, of the fluid pump in order to be able to develop a greater lever effect on the rotor 4 which can be tilted around the rotational point, situated in the volute 1b, of the mechanical and/or hydrodynamic bearing 10a, 10b. The magnetic bearing 8a, 8b is, furthermore, configured in this embodiment such that the rotor 4, during operation of the fluid pump, is always pressed into the mechanical and/or hydrodynamic bearing in order to minimise a bearing gap between the bearing components 10a and 10b. In contrast to the first embodiment, in the second embodiment, the rotor 4 is hence not pressed towards the fluid inlet 2 but into the volute 1c towards the fluid outlet 3. According to how strong the pretension of the rotor 4 directed towards the fluid outlet 3 is adjusted counter to the fluid flow by means of the magnetic bearing 8a, 8b, relieving the load of the mechanical and/or hydrodynamic bearing 10a, 10b occurs in the fluid pump, according to the second embodiment, during operation. As also in the first embodiment, in the second embodiment no contact between the safety bearing components 11a and 11b takes place in normal operation of the fluid pump. The safety bearing 11a, 11b retains the rotor 4 by means of the radial and axial delimiting elements 12 and 13 only in the case of a great deflection of the rotor 4 out of its ideal position on the central axis 5 because of external interfering forces.

A further difference from the first embodiment resides in the arrangement of the conveying elements 7. These are situated in the central region of the hollow-cylindrical interior 1a and are configured such that they accelerate the fluid in the axial direction parallel to the central axis. On the basis of the arrangement of the conveying elements 7 in the central region of the interior 1a, the conveying elements 7 can abut earlier against the inner wall 1c in the case of a great deflection of the rotor 4 from its ideal position than is the case in the first embodiment in FIG. 1. Therefore also the radial bearing gap between the second safety bearing component 11b and the radial delimiting element 12 is configured to be smaller than in FIG. 1 in order to avoid contact of the conveying elements 7 on the inner wall 1c. The radial spacing between the safety bearing component 11b and the delimiting element 12 is however greater also in FIG. 2 than the clearance of the conveying elements 7 relative to the inner wall 1c.

Figure 3:
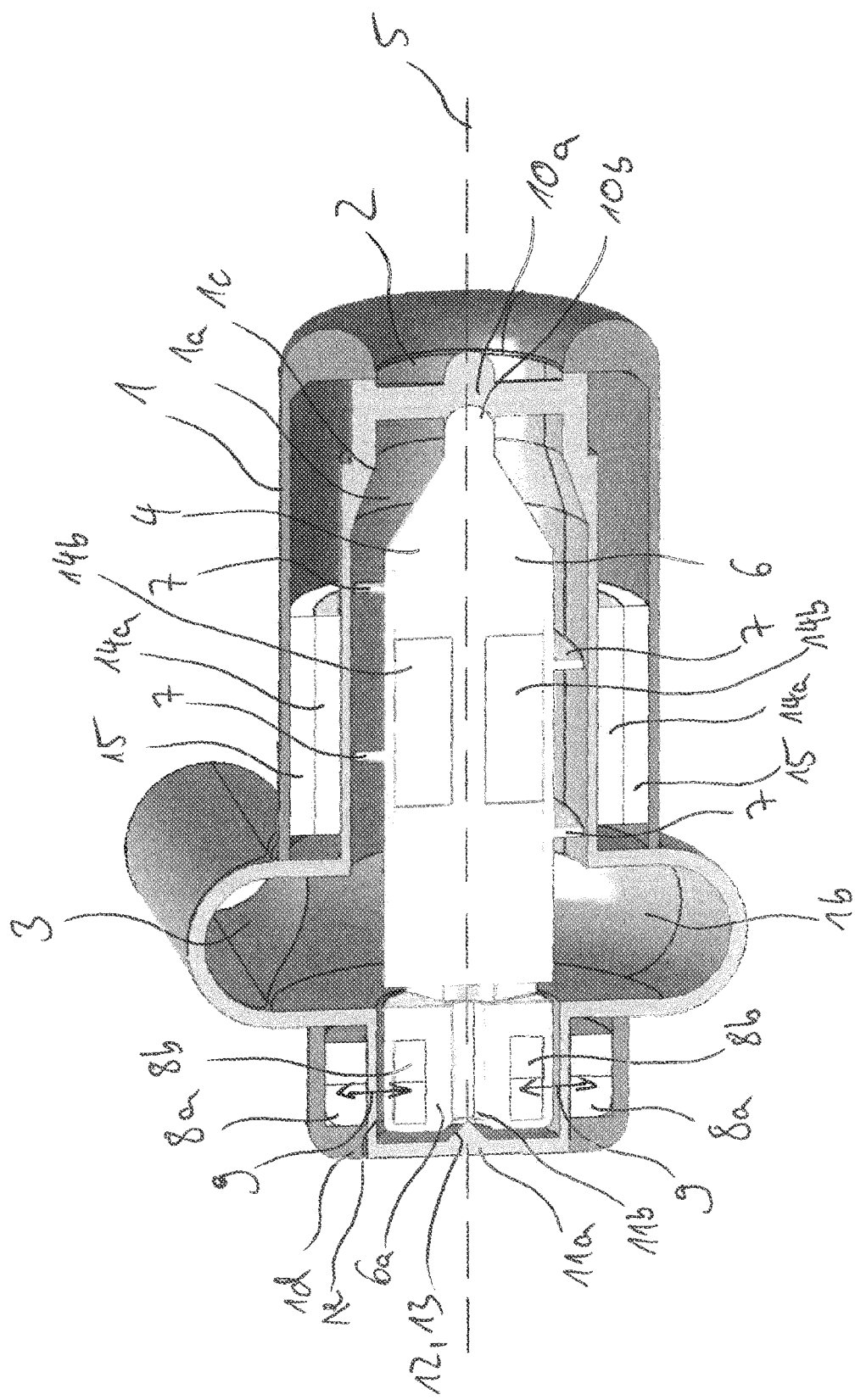

FIG. 3 shows a third embodiment of a fluid pump according to the invention in an axial section view. In the third embodiment, as in the first embodiment, the mechanical and/or hydrodynamic bearing 10a, 10b is disposed in the region of the fluid inlet 2. Differently from the first embodiment, the safety bearing 11a, 11 b is now disposed on a side of the volute 1b orientated away from the fluid inlet 2, outside a primary fluid path leading from the fluid inlet 2 to the fluid outlet 3. For this purpose, on a side of the volute 1b orientated away from the fluid inlet 2, both the housing 1 has a likewise hollow-cylindrical housing extension 1d and the rotor body 6 has a rotor body extension 6a. The first safety bearing component 11a connected rigidly to the housing extension 1d has a mandrel-shaped configuration and engages in a second safety bearing component 11b, configured as boring tapering in the direction of the volute 1b in the rotor body extension 6a and hence delimits a translatory movement of the rotor 4 in the axial direction and a rotational movement of the rotor 4 about the mechanical and/or hydrodynamic bearing 10a, 10b.

Also the magnetic bearing 8a, 8b is disposed, in the second embodiment, on the side of the volute 1b orientated away from the fluid inlet 2, the housing magnet 8a being situated in the housing extension 1d and the rotor magnet 8b in the rotor body extension 6a. Because of the large axial spacing relative to the mechanical and/or hydrodynamic bearing 10a, 10b because of the position outside the volute 1b, the magnetic bearing 8a, 8b can exert a greater lever effect on the rotor 4 for radial fixing of the rotor 4. A further advantage of the fluid pump, according to the third embodiment, resides in particular in the fact that a smaller magnetic bearing can be used since it is possible to dispose the housing magnet 8a and the rotor magnet 8b at a smaller distance from each other and to increase the magnetic force in this way. A smaller spacing between the housing magnet 8a and the rotor magnet 8b is possible since, between the inner wall 1e of the housing extension 1d and the rotor body extension 6a, a smaller spacing than in the region of the primary fluid path can be made possible since no conveying elements need be accommodated.

The conveying elements 7 in the third embodiment, as in the second embodiment, are disposed in the central region of the interior 1a. However in FIG. 3, the axial spacing relative to the mechanical and/or hydrodynamic bearing 10a, 10b is so large that the radial bearing gap in the safety bearing 11a, 11 b can have a larger configuration than in FIG. 2 without the conveying elements 7 abutting against the inner wall 1c of the housing 1 before contact of the safety bearing components 11a, 11b.

Figure 4:
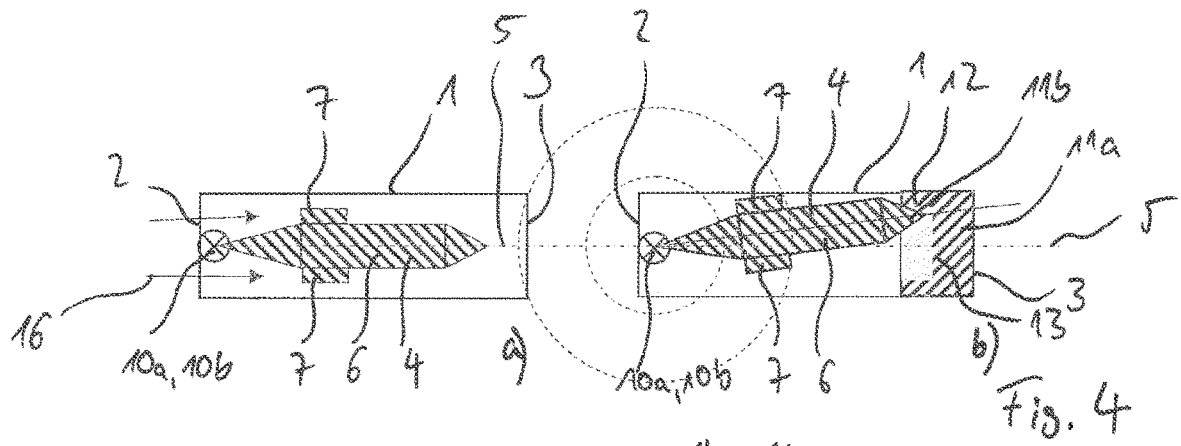

FIG. 4 shows a diagram which illustrates a limit stop protection by the safety bearing 11a, 11b. In FIG. 4a), the rotor 4 is situated in its ideal position, i.e. the axis of rotation of the rotor 4 and the central axis 5 coincide. In FIG. 4b), the rotor 4 is tilted relative to the central axis 5. The mechanical and/or hydrodynamic bearing 10a, 10b is disposed in the region of the fluid inlet 2, through which a fluid flow 16 enters into the fluid pump, and represents a rotational point for the rotor 4. Tilting of the rotor 4 relative to the central axis 5 is delimited by the bearing gap in the safety bearing 11a, 11b, the position of the conveying elements 7 and the restoring force of the magnetic bearing. Contact of the conveying elements 7 should absolutely be avoided as this rapidly leads to great damage in the fluid pump, which has a negative effect on the patient. As interfering forces and interfering moments, in particular radial fluid forces, tilting moments by fluid forces and radial forces and tilting moments by g-forces and also gyroscopically induced tilting moments occur. The g-force provides the strongest quasi stationary component.

As free as possible tilting of the rotor 4 without the conveying element 7 contacting the housing 1 can be achieved for example by a special geometry of the conveying elements 7. The available tilting angle of the rotor 4 is defined geometrically by the clearance of the conveying elements 7 and the spacing from the bearing point of the mechanical and/or hydrodynamic bearing 10a, 10b. This tilting angle is maximised when the conveying elements 7 are disposed as closely as possible to the bearing point or spherically about the latter. Conveying elements 7a provided with a spherical outer contour, as illustrated for example in FIG. 6, can hence avoid the tilting problem for the most part. The clearance in this case is entirely independent of the tilting angle of the rotor 4 and the uncontrolled contact of the rotor 4 can be prevented with a simple safety bearing 11a, 11b. The necessary bearing rigidity of the magnet bearing 8a, 8b of the fluid pump is then defined exclusively by external forces and moments in cooperation with the available tilting angle of the rotor 4.

Figure 5:
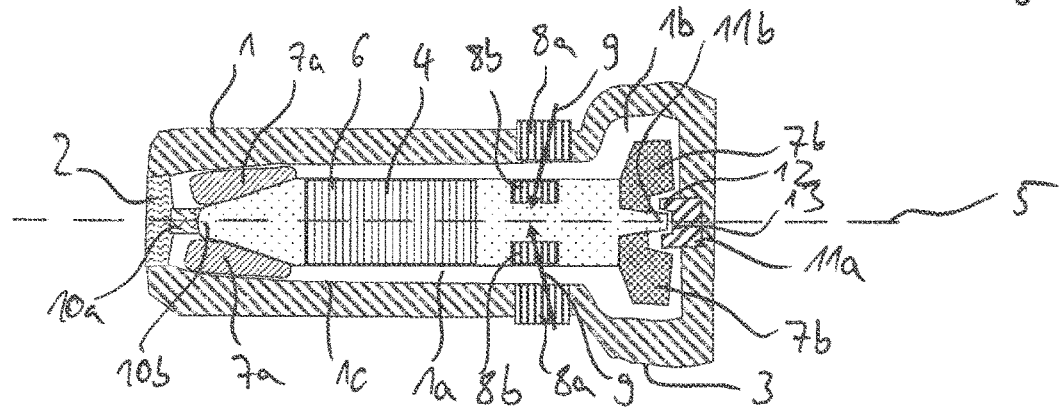

FIG. 5 shows a fourth embodiment of a fluid pump according to the invention in an axial section view. The mechanical and/or hydrodynamic bearing 10a, 10b is disposed in the region of the fluid inlet 2, as in FIGS. 1 and 3. The conveying elements 7 are disposed directly adjacent to the mechanical and/or hydrodynamic bearing 10a, 10b and partially overlap the latter. Furthermore, the outer contour of the conveying elements 7a orientated towards the inner wall 1c is adapted to a course of the inner wall 1c over essentially the entire axial length of the conveying elements 7a so that a small clearance relative to the inner wall 1c is produced over the entire course of the axial length of the conveying elements 7a. Because of the overlapping of the conveying elements 7a with the mechanical and/or hydrodynamic bearing 10a, 10b, the conveying elements 7a can have a larger configuration and receive and accelerate the fluid flow earlier at the fluid inlet 2. The illustrated conveying elements 7 can therefore pump the fluid very efficiently through the housing 1. Furthermore, the conveying elements 7a overlapping the mechanical and/or hydrodynamic bearing 10a, 10b can wash around the mechanical and/or hydrodynamic bearing 10a, 10b, and thus support the functional capacity of the bearing 10a, 10b. In addition, the inner wall 1c extends at an acute angle to the central axis 5 which opens out from the fluid inlet 2. Despite the small clearance, this prevents early contact of the conveying elements 7a on the inner wall 1c. The safety bearing 11a, 11 b disposed in the volute 1b has a bearing gap which prevents, on the one hand, contact of the conveying elements 7a on the wall 1c and, on the other hand, is large enough to keep shearing forces in the bearing 11a, 11b low and thus to prevent fluid damage.

Differently from the preceding embodiments, the fluid pumps of the fourth and fifth embodiment have alternative or additional conveying elements 7b in the volute 1b. These serve for the purpose of conveying the fluid more quickly out of the fluid pump tangentially through the fluid outlet 3 and hence once again increase the efficiency of the fluid pump or represent a purely radial configuration as single buckets in which in general the spacings between buckets and housing can have a larger configuration than in the axial or semiaxial pump concepts described further back.

Figure 6:
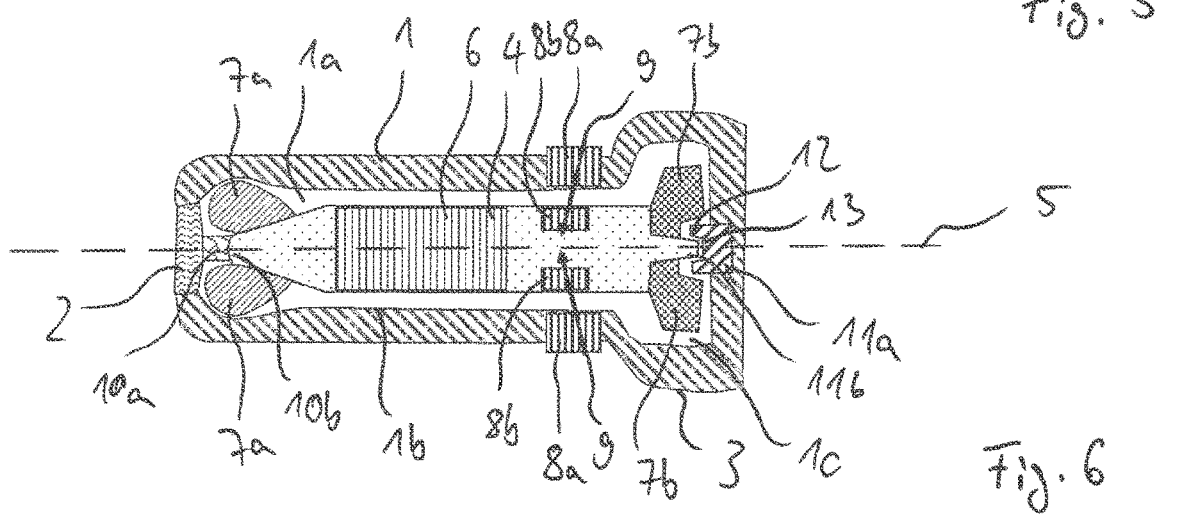

FIG. 6 shows a fifth embodiment of a fluid pump according to the invention in an axial section view. The fluid pump of the fifth embodiment comprises a combination of conveying elements 7a and inlet geometry which was mentioned already in the description of FIG. 4. The fifth embodiment of FIG. 6 differs from the fourth embodiment of FIG. 5 by the inner wall 1c around the mechanical and/or hydrodynamic bearing 10a m 10b having a spherical configuration. This makes it possible for the rotor 4 to have a large tilting angle about the mechanical and/or hydrodynamic bearing 10a, 10b. The conveying elements 7a here are also adapted in their contour orientated towards the inner wall 1c to the course of the inner wall 1c so that a small clearance is produced over a large proportion of the axial length of the conveying elements 7a. Because of the spherical course of the inner wall 1c, early contact of the conveying elements 7a despite the small clearance is avoided. Contact is then only effected in the safety bearing 11a, 11b. Furthermore, also in the fifth embodiment of FIG. 6, as already in the fourth embodiment of FIG. 5, alternative or additional conveying elements 7b are disposed in the volute 1b and make it possible to convey the fluid more quickly out of the pump through the fluid outlet 3.

To clarify the use of and to hereby provide notice to the public, the phrases "at least one of <A>, <B>, . . . and <N>" or "at least one of <A>, <B>, . . . or <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A fluid pump for conveying a fluid comprising:
a housing with a fluid inlet and a fluid outlet,
a rotor which is disposed rotatably about an axis of rotation in the housing, and
a rotor body and at least one conveying element connected rigidly to the rotor body in order to convey the fluid from the fluid inlet to the fluid outlet,
the rotor being mounted in the housing radially to the axis of rotation by means of a passive magnetic bearing and also axially and radially by means of a mechanical and/or hydrodynamic bearing disposed on the inlet side or outlet side,
wherein a safety bearing being disposed on one side of the rotor situated opposite the mechanical and/or hydrodynamic bearing, wherein the safety bearing has a first safety bearing component connected rigidly to the rotor and a second safety bearing component connected rigidly to the housing, during operation of the fluid pump, an axial and radial spacing between the first and the second safety bearing component being greater than a radial minimal spacing between the rotor and the housing, and the safety bearing being equipped to restrict deflection of the rotor in the radial direction inside the housing.

2. The fluid pump of claim 1, wherein the safety bearing is configured such that, during operation of the fluid pump, there is, between the first and the second safety bearing component, an axial spacing ≥10 µm and/or ≤500 µm and a radial spacing ≥50 µm and/or ≤1,000 µm.

3. The fluid pump of claim 1, wherein the safety bearing is disposed outside a primary fluid path leading from the fluid inlet to the fluid outlet.

4. The fluid pump of claim 3, wherein the safety bearing is disposed on one side of a volute of the housing orientated away from the mechanical and/or hydrodynamic bearing.

5. The fluid pump of claim 1, wherein the conveying element is disposed in a region of the rotor body adjacent to the mechanical and/or hydrodynamic bearing.

6. The fluid pump of claim 1, wherein the conveying element is disposed on the rotor body such that the conveying element overlaps the mechanical and/or hydrodynamic bearing radially to the axis of rotation.

7. The fluid pump of claim 1, wherein the conveying element is disposed in a region of the rotor body in which a spacing between a surface of the rotor body and the housing is greater than a minimal spacing between the surface and the housing.

8. The fluid pump of claim 7, wherein the conveying element is disposed in a volute of the housing.

9. The fluid pump of claim 1, wherein the conveying element has, on one side orientated towards the housing, an axial section contour which is adapted to an inner axial section contour of the housing on a side of the housing orientated towards the conveying element so that a radial spacing between the conveying element and the housing, along at least one region of the conveying element, is essentially constant in the axial direction.

10. The fluid pump of claim 9, wherein the radial spacing between the conveying element and the housing, along at least one region of the conveying element is least ≥40% of a length of the conveying element in the axial direction.

11. The fluid pump of claim 9, wherein the axial section contour of the conveying element and the inner axial section contour of the housing have corresponding spherical curves.

12. The fluid pump of claim 1, wherein the magnetic bearing is disposed in the axial direction on a side of the rotor body situated towards the safety bearing.

13. The fluid pump of claim 1, wherein the magnetic bearing has at least one first and one second magnet, the first magnet being disposed in the housing and the second magnet being disposed in the rotor body, the second magnet opposite the first magnet being offset in the axial direction relative to the mechanical and/or hydrodynamic bearing so that the rotor body is pretensioned in the axial direction counter to a fluid flow.

14. The fluid pump of claim 1, wherein the mechanical and/or hydrodynamic bearing has a first bearing component connected rigidly to the rotor and a second bearing component connected rigidly to the housing, and the magnetic bearing is configured such that, during operation of the fluid pump, a spacing between the first and the second bearing component is minimised.

15. The fluid pump of claim 14, wherein the magnetic bearing is configured such that, during operation of the fluid pump, the spacing between the first and the second bearing component is smaller than the axial and/or radial spacing between the first safety bearing component and the second safety bearing component.

16. The fluid pump of claim 1, wherein the fluid pump is an axial flow pump or a radial flow pump or a combination of axial flow- and radial flow pump.

17. The fluid pump of claim 1, wherein the first and/or the second safety bearing component comprise a ceramic, polymeric, metallic and/or monocrystalline material or consist thereof, and/or wherein a first and/or second bearing component of the mechanical and/or hydrodynamic bearing comprise a ceramic, polymeric, metallic and/or monocrystalline material or consist thereof.

18. The fluid pump of claim 1, wherein the first and/or the second safety bearing component has a coating which inhibits wear and tear and/or reduces blood damage, and/or in that wherein a first and/or second bearing component of the mechanical and/or hydrodynamic bearing has a coating which inhibits wear and tear and/or reduces blood damage.

* * * * *